US012685507B2

(12) United States Patent
Bagley et al.

(10) Patent No.: US 12,685,507 B2
(45) Date of Patent: Jul. 21, 2026

(54) STETHOSCOPE SYSTEMS AND ASSEMBLIES

(71) Applicant: GlobalMedia Group, LLC, Scottsdale, AZ (US)

(72) Inventors: Phnam Bagley, San Francisco, CA (US); Joseph Benjamin Moak, San Carlos, CA (US); Yuri Viacheslav Litvinov, San Carlos, CA (US); Daniel Corey Wiggins, Ventura, CA (US); Nadezhda Kutyreva, San Mateo, CA (US); Thomas Herbert Grimm, San Jose, CA (US); Arne Lang-Ree, San Jose, CA (US); Shailendra Shashikant Govardhan, Los Gatos, CA (US); Mark Adrian Stubbs, Los Gatos, CA (US)

(73) Assignee: GLOBALMED HOLDINGS, LLC, Scottsdale, AZ (US)

( * ) Notice: Subject to any disclaimer, the term of this patent is extended or adjusted under 35 U.S.C. 154(b) by 708 days.

(21) Appl. No.: 17/866,239

(22) Filed: Jul. 15, 2022

(65) Prior Publication Data

US 2024/0016468 A1     Jan. 18, 2024

(51) Int. Cl.
| | |
|---|---|
| *H04R 1/46* | (2006.01) |
| *A61B 7/04* | (2006.01) |
| *G06F 1/16* | (2006.01) |
| *G06F 1/26* | (2006.01) |
| *G06F 1/3206* | (2019.01) |
| *H01H 19/14* | (2006.01) |

(52) U.S. Cl.
CPC ................ *A61B 7/04* (2013.01); *G06F 1/163* (2013.01); *G06F 1/1632* (2013.01); *G06F 1/1698* (2013.01); *G06F 1/266* (2013.01); *G06F 1/3206* (2013.01); *H01H 19/14* (2013.01); *H04R 1/46* (2013.01)

(58) Field of Classification Search
CPC ................................... H04R 1/46; A61B 7/04
See application file for complete search history.

(56) References Cited

U.S. PATENT DOCUMENTS

| | | | |
|---|---|---|---|
| 9,414,803 B1 * | 8/2016 | Naqvi ...................... | H04W 4/80 |
| 2012/0310115 A1 | 12/2012 | Bedingham et al. | |
| 2014/0270218 A1 * | 9/2014 | Wang ....................... | A61B 7/04 381/67 |
| 2020/0205770 A1 | 7/2020 | Friedman et al. | |
| 2021/0169203 A1 * | 6/2021 | Woolery ................ | A45C 15/00 |
| 2021/0345991 A1 | 11/2021 | Adler et al. | |
| 2022/0094207 A1 * | 3/2022 | Truettner .............. | H02J 7/0013 |

OTHER PUBLICATIONS

Patent Cooperation Treaty, International Search Report and Written Opinion Received in PCT Application No. PCT/US2023/027844, dated Feb. 20, 2024.

* cited by examiner

*Primary Examiner* — Ping Lee
(74) *Attorney, Agent, or Firm* — SNELL & WILMER L.L.P.

(57) ABSTRACT

A chest piece for a wireless stethoscope system can be configured to receive, from the accelerometer, motion data; determine, based on the motion data, that the chest piece has experienced no moment for a time threshold; and command the chest piece to enter a sleep mode that consumes less power in response to determining that no moment has occurred for the time threshold.

18 Claims, 13 Drawing Sheets

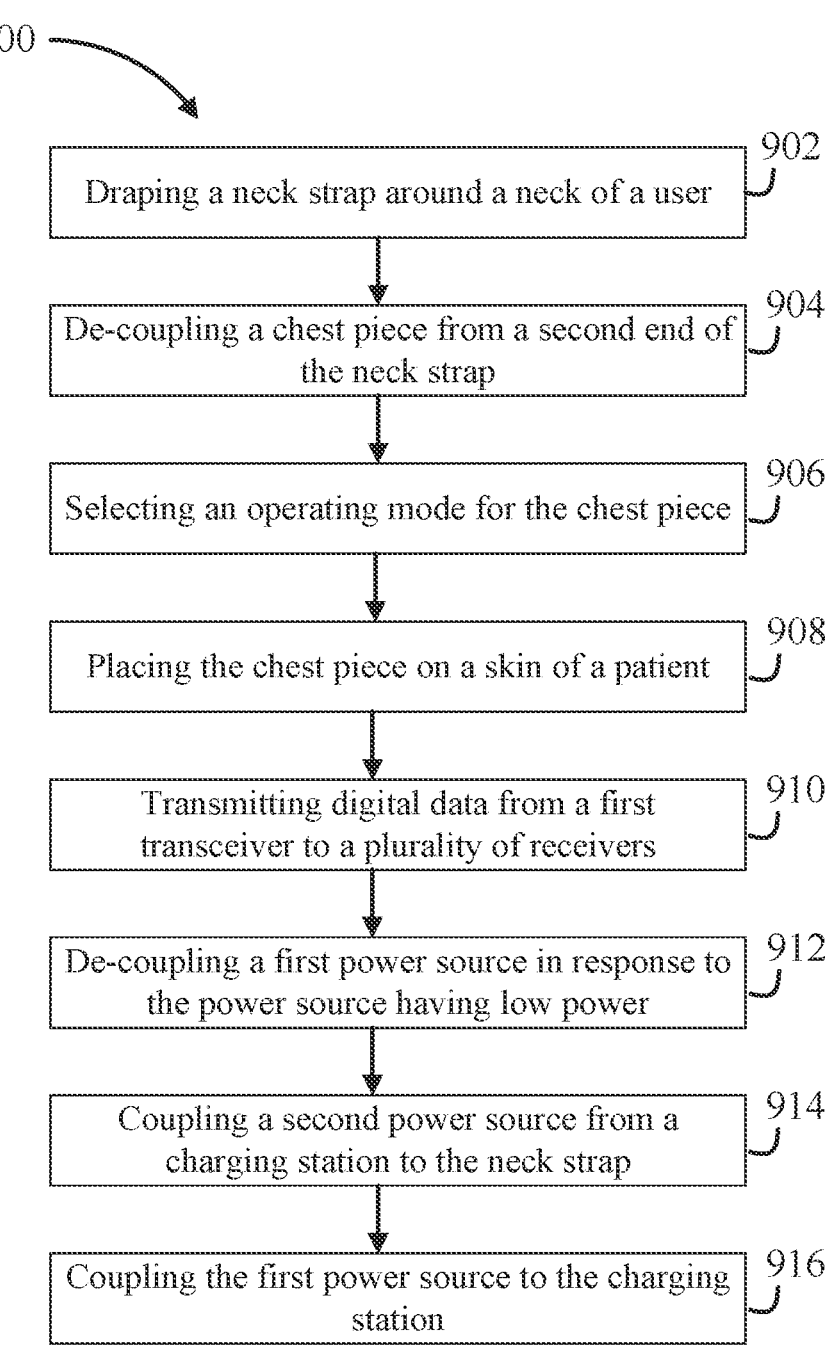

900

902 Draping a neck strap around a neck of a user

904 De-coupling a chest piece from a second end of the neck strap

906 Selecting an operating mode for the chest piece

908 Placing the chest piece on a skin of a patient

910 Transmitting digital data from a first transceiver to a plurality of receivers 912 De-coupling a first power source in response to the power source having low power 914 Coupling a second power source from a charging station to the neck strap 916 Coupling the first power source to the charging station

FIG. 9

STETHOSCOPE SYSTEMS AND ASSEMBLIES

FIELD

The present disclosure generally relates to stethoscope systems and assemblies, and more specifically to an electronic stethoscope that provides separate members for auscultation and audible play that are in wired and/or wireless communication whilst cancelling out outside ambient sounds.

BACKGROUND

With the many types of stethoscopes known in the prior art, most are electronic. Some electronic stethoscopes have digital readouts while others offer separate auscultation devices and earpieces. What is needed is an electronic stethoscope that provides separate auscultation from audible information derived from a patient. The stethoscope should communicate via encrypted wireless transmission. The stethoscope should ideally provide more than one auditory auscultation stream.

SUMMARY

A chest piece is disclosed herein. In various embodiments, the chest piece can comprise: a housing assembly; an accelerometer disposed in the housing assembly; a plurality of lights disposed in the housing assembly; a transducer disposed in the housing assembly; a transceiver disposed in the housing assembly; a controller for electrical communication with the accelerometer, the transducer, and the transceiver, the controller configured to: receive, from the accelerometer, motion data; determine, based on the motion data, that the chest piece has experienced no moment for a time threshold; and command the chest piece to enter a sleep mode that consumes less power in response to determining that no moment has occurred for the time threshold.

In various embodiments, the housing assembly further comprises a transparent membrane positioned over the plurality of lights.

In various embodiments, the housing assembly further comprise a rotary ring, a first limit switch and a second limit switch, the controller configured to change a mode of operation of the chest piece in response to the second limit switch detecting a presence of the rotary ring after the first limit switch previously detected the presence of the rotary ring.

In various embodiments, the chest piece further comprises: a first prod and a second prod positioned vertically; and a cable retention assembly configured to apply a retention force to a cable in response to the cable being electrically coupled to an electrical port of the chest piece.

In various embodiments, the chest piece further comprises a power supply disposed in the housing assembly, the power supply in electrical communication with the controller. The chest piece can further comprise an electrical connector configured to couple to a neck strap of a wireless stethoscope system.

A stethoscope system is disclosed herein. In various embodiments, the stethoscope system can comprise: a power source; a main housing comprising a neck strap extending from a first end to a second end, the first end configured to couple to the power source, the main housing comprising a first transceiver; a chest piece configured to removably couple to the second end of the neck strap, the chest piece comprising a second transceiver; a fully assembled configuration having the power source and the chest piece both coupled to the neck strap, the power source configured to charge a power supply in the chest piece in response to being in the fully assembled configuration; and an operable configuration having the power source coupled to the neck strap and the chest piece being de-coupled from the neck strap, the neck strap configured to wrap loosely around a user's neck, and the chest piece configured to convert auscultation signals to digital signals for wireless transmission from the second transceiver to the first transceiver.

In various embodiments, the stethoscope system can further comprise a plurality of headsets, the chest piece configured to wirelessly transmit the digital signals to the plurality of headsets in the operable configuration.

In various embodiments, the chest piece is configured to transmit the digital signals to a plurality of transceivers.

In various embodiments, the stethoscope system can further comprise a charging system, the charging system including a plurality of charge ports, each charge port in the plurality of charge ports configured to receive the power source. The stethoscope system can further comprise a plurality of the power source, each power source in the plurality of the power source configured to charge in a respective charge port in response to not being in use. Any power source in the plurality of the power sources is swappable with the power source in response to the power source running low on a state of charge.

A chest piece is disclosed herein. In various embodiments, the chest piece comprises: a bell with a transducer; a housing assembly having an upper housing, a lower housing, a rotary ring, and a cap, the lower housing disposed between the upper housing and the bell with the transducer; and a clamping mechanism disposed within the housing assembly, the clamping mechanism disposed proximate a first electrical connector, the clamping mechanism configured to retain a second electrical connector configured to couple to the first electrical connector in response to coupling the second electrical connector to the first electrical connector.

In various embodiments, the first electrical connector is an electrical socket, and wherein the second electrical connector is an electrical port.

In various embodiments, the chest piece further comprises a printed circuit board disposed within the housing assembly, the printed circuit board having a controller, a plurality of lights, a power supply, and a transceiver.

A method of using a wireless stethoscope system is disclosed herein. In various embodiments, the method comprises: draping a neck strap around a neck of a user, the neck strap coupled to a power source on a first end and a chest piece on a second end; de-coupling the chest piece from the second end; selecting an operating mode for the chest piece; placing the chest piece on a skin of a patient; and transmitting digital data from a first transceiver to a plurality of receivers.

In various embodiments, the plurality of receivers can each be associated with a respective headset in a plurality of headsets.

In various embodiments, the method further comprises de-coupling the power source in response to the power source having low power; and coupling a second power source to the first end of the neck strap. The method can further comprise de-coupling the second power source from a charging station having plurality of power sources prior to coupling the second power source to the neck strap. The method can further comprise coupling the power source to the charging station.

A stethoscope system is disclosed herein. In various embodiments, the stethoscope system comprises: a neck strap comprising a first controller, a first transceiver, and a first memory, the first transceiver electrically coupled to a first electrical connector; a chest piece comprising a second controller, a second transceiver, a second memory, and a transducer configured to detect auscultation signals, the second transceiver electrically coupled to a second electrical connector, wherein in response to coupling the first electrical connector to the second electrical connector, wherein the following operations can be performed by the stethoscope system: the first transceiver sends a first command with neck strap data to the second transceiver electrically; the second transceiver sends acknowledgement of the first command to the first transceiver electrically; the second transceiver sends a second command with chest piece data to the first transceiver electrically; the first transceiver sends a second acknowledgement of the second command to the second transceiver electrically; the first transceiver determines whether the first transceiver and the second transceiver are paired; the first transceiver sends a pairing command in response to the first transceiver and the second transceiver not being paired; the second transceiver sends a third acknowledgement of the pairing command electrically; the second transceiver detects a peripheral beacon of the first transceiver electronically; the first transceiver sends a security passkey command to the second transceiver electronically; and the second transceiver receives the security passkey command electronically, verifies a security passkey from the security passkey command, and send a fourth acknowledgment to the first transceiver electrically.

In various embodiments, the operations further comprise: the second transceiver sends a second security passkey command to the first transceiver electronically; and the first transceiver receives the second security passkey command electronically, verifies a second security passkey of the second security passkey command, and sends a fifth acknowledgement to the second transceiver electrically.

In various embodiments, the operations further comprise generating long term keys for future connections.

A cable retention assembly is disclosed herein. In various embodiments, the cable retention assembly comprises: a housing defining a cable aperture extending axially into the housing and a retention aperture oriented substantially orthogonal to the cable aperture and opening into the cable aperture; and a clamping mechanism disposed at least partially within the retention aperture, the clamping mechanism pivotably coupled to the housing and configured to apply a retention force on a cable in response to the cable being inserted into the cable aperture.

In various embodiments, the clamping mechanism comprises an engagement portion configured to apply the retention force.

In various embodiments, the clamping mechanism comprises a spring configured to bias the clamping mechanism at least partially within the retention aperture.

A chest piece is disclosed herein. In various embodiments, the chest piece comprises: a housing; a diaphragm coupled to the housing; and a clamping mechanism disposed within the housing, the clamping mechanism pivotably coupled to the housing and configured to apply a retention force on a cable in response to the cable being inserted into a cable port within the housing.

The forgoing features and elements may be combined in various combinations without exclusivity, unless expressly indicated herein otherwise. These features and elements as well as the operation of the disclosed embodiments will become more apparent considering the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosures, however, may best be obtained by referring to the detailed description and claims when considered in connection with the drawing figures, wherein like numerals denote like elements.

FIG. 9 illustrates a method of operating a stethoscope system, in accordance with various embodiments.

DETAILED DESCRIPTION

Figure 1A:
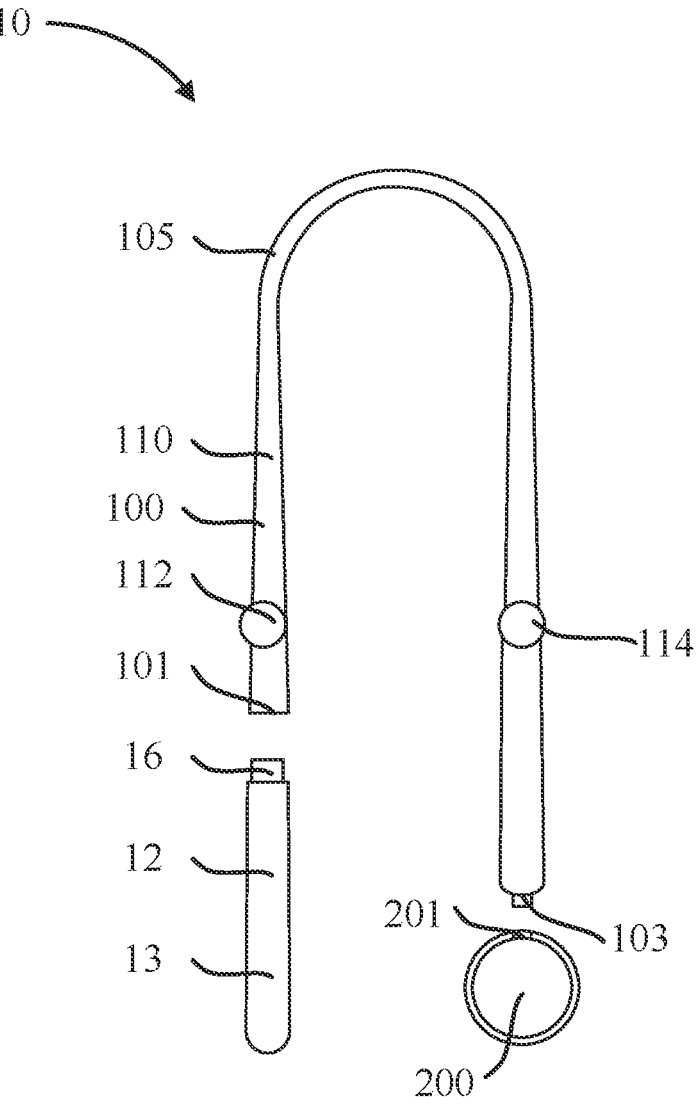
FIG. 1A illustrates a front view of a stethoscope system in a disassembled state, in accordance with various embodiments.

The detailed description of exemplary embodiments herein refers to the accompanying drawings, which show exemplary embodiments by way of illustration and their best mode. While these exemplary embodiments are described in sufficient detail to enable those skilled in the art to practice the disclosures, it should be understood that other embodiments may be realized and that logical, chemical, and mechanical changes may be made without departing from the spirit and scope of the disclosures. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Systems, methods, and devices are disclosed herein for retaining a cable within a respective port. As used herein, an "electrical connector" may refer to any electromechanical device capable of transferring electrical signals from one device to another. Any electrical connector connection disclosed herein may be first component with a plug and a second component with a socket, or vice versa. The present disclosure is not limited in this regard. For, example and without limitation, an electrical connector may refer to a High-Definition Multimedia (HDMI) connector, display connectors, Serial Advanced Technology Attachment (SATA) connectors, Universal Serial Bus (USB) connectors, firewall Institute of Electrical and Electronics Engineers (IEEE) connectors, an audio jack, or any other suitable device.

The systems and methods disclosed herein may enable communication between devices without connection to the Internet or other networks using an SCS. A standardized communication system ("SCS") may be operable on the computing devices of the present disclosure. The SCS may comprise any combination of hardware and/or software. The SCS may utilize existing physical components of the device, such as 802.11 or 802.2(2) wireless chips and Bluetooth® systems in order to communicate with other devices. The SCS may be suitable for any communication protocol, such as IP, TCP/UDP, Bluetooth®, raw Manchester encoding, and any other form of wireless communication.

With reference now to FIG. 1A, a front view of a stethoscope system 10 (e.g., an electronic wireless stethoscope system) is illustrated, in accordance with various embodiments. The stethoscope system 10 comprises a power source 12 (e.g., a rechargeable battery, a supercapacitor, or the like), a main housing 100 (e.g., a neck strap), and a chest piece 200. In various embodiments, the power source 12 is a rechargeable battery (e.g., a rechargeable lithium ion battery). The power source 12 is configured to removably couple to the main housing 100. Similarly, the chest piece 200 is configured to removably couple to the main housing 100.

The power source 12 comprises a housing 13 and an electrical connector 16. The housing 13 is configured to house elements of the power source (e.g., a plurality of cells, each having an anode and a cathode for a rechargeable battery). The electrical connector 16 is configured to be coupled to a first electrical connector 101 of the main housing 100. Thus, the power source 12 configured to provide power to electrical components in the main housing 100 and/or the chest piece 200 in a fully assembled state. A "fully assembled state" as disclosed herein, refers to the power source 12 and the chest piece 200 both being connected to the main housing 100. In an "operable state", the chest piece is de-coupled from the main housing 100 and the power source 12 remains coupled to the main housing 100 as described further herein.

The main housing 100 comprises a case 110. The case 110 is configured to house various components. In various embodiments, the case 110 may be made from a polymeric material or the like configured to provide an ergonomic feel for a user. Although described as a polymeric material, any type of material known in the art is within the scope of this disclosure.

The main housing 100 comprises a first electrical connector 101 and a second electrical connector 103. In various embodiments, the main housing 100 is a neck strap 105. Although illustrated as having the main housing 100 as a neck strap 105, the present disclosure is not limited in this regard. For example, the main housing could be a wrist band, a shoulder strap, or the like, in accordance with various embodiments. In various embodiments, the first electrical connector 101 is disposed on a first end of the neck strap 105 and the second electrical connector 103 is disposed on a second end of the neck strap 105, the second end being opposite the first end.

In this regard, in a fully assembled state where the stethoscope system 10 is not in use, the neck strap 105 may be draped on a user's (e.g., a doctor's) neck with the power source 12 on one side of the user's neck and the chest piece 200 on the other side of the user's neck in a similar manner to typical stethoscope.

In various embodiments, the neck strap 105 provides easy access to a user (e.g., a doctor). For example, the neck strap 105 may be configured to hang loosely around a user's neck, allow the user easy access to the earbuds 112, 114 and the chest piece 200. In this regard, the neck strap 105 may provide a similar feel to non-electronic stethoscopes with additional functionality as described further herein.

The chest piece 200 comprises an electrical connector 201. The electrical connector 201 is configured to removably couple to the second electrical connector 103 of the main housing 100. In various embodiments, in response to coupling to the second electrical connector 103 of the main housing 100, the chest piece 200 is configured to charge and/or to wirelessly pair with the main housing, in accordance with various embodiments as described further herein. In the operable state, the chest piece 200 is configured to absorb physical auscultation from any location while touching the skin of a patient. In the operable state, as described further herein, the chest piece 200 is configured to convert auscultation data (e.g., auscultation signals) to digital data (e.g., digital signals) representative of the auscultation signals for wireless transmission to the main housing 100 and/or any secondary location configured to receive digital data wirelessly, such as a computer, a tablet, a cell phone, a second set of earbuds, etc. The present disclosure is not limited with regard to the secondary location. In various embodiments, the wireless transmission of the digital data allows for monitoring of the auscultation data of a patient in real time (e.g., via the earbuds 112, 114), and later analysis of the auscultation data (e.g., via the transmitted data to the secondary location).

Figure 2:
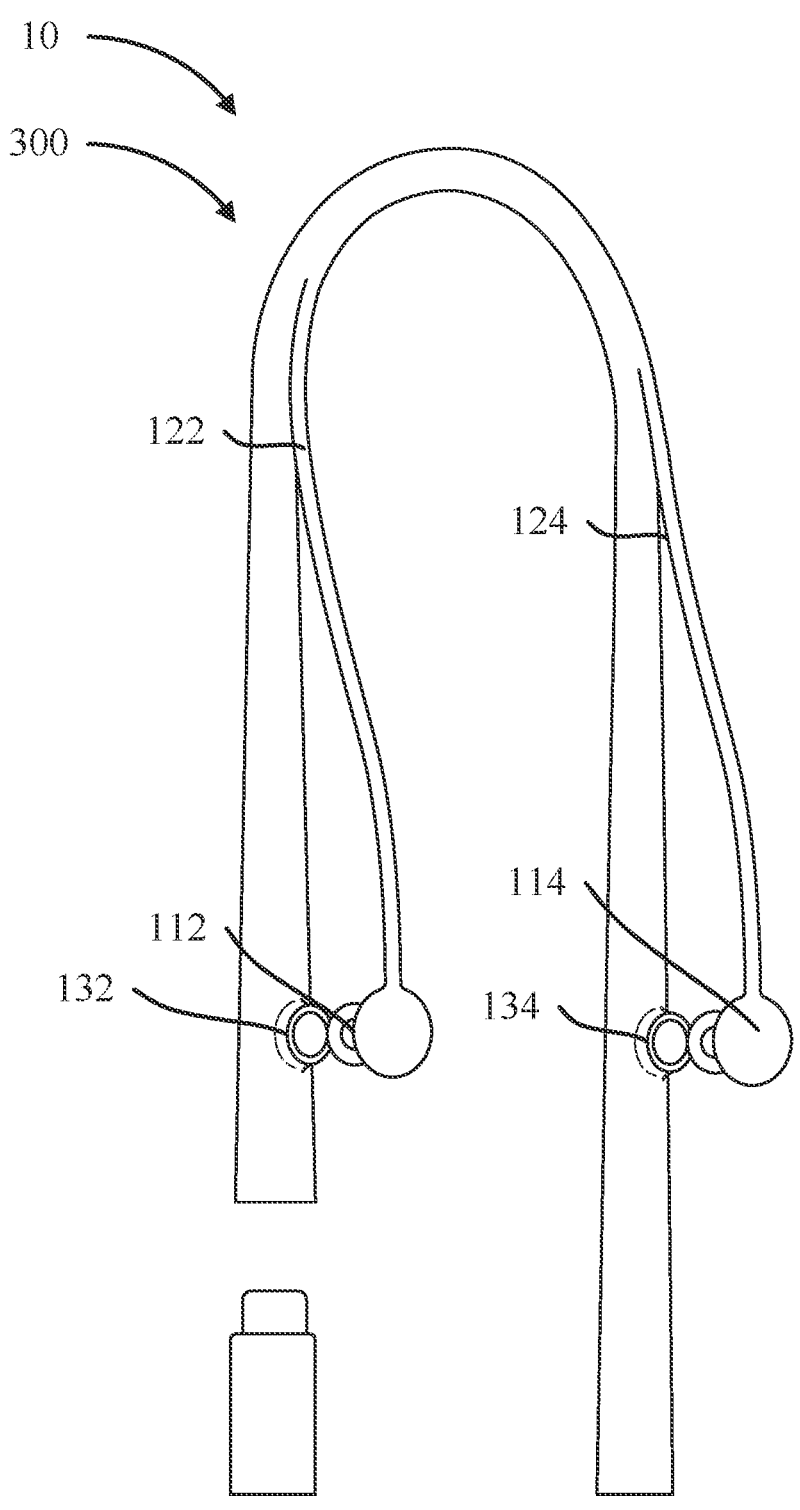
FIG. 2 illustrates a portion of a perspective view of a stethoscope system, in accordance with various embodiments.

The stethoscope system 10 further comprises earbuds 112, 114. In various embodiments, the earbuds 112, 114 may be wired within main housing 100 and configured to extend to a user's ear (e.g., integral with the main housing 100). For example, with brief reference to FIG. 2, cable 122 may extend from main housing 100 to earbud 112 and cable 124 may extend from the main housing 100 to earbud 114 in a wired configuration 300 without audio jacks/ports of the stethoscope system 10, in accordance with various embodiments. In various embodiments, in the wired configuration 300, the main housing 100 further comprises earbud ports 132, 134, each configured to receive a respective earbud 112, 114 to hold the respective earbud 112, 114 when the stethoscope system is not in use.

In various embodiments, the earbuds 112, 114 may be removably coupled to the main housing 100. For example, the earbuds 112, 114 may comprise wired earbuds configured to electrically couple to electrical components within the main housing 100 or the earbuds 112, 114 may be wireless earbuds configured to couple to electrical components within the main housing 100 for charging, pairing, and/or storage purposes. Thus, the stethoscope system 10 may be configured for wired or wireless earbuds. The present disclosure is not limited in this regard.

Figure 1B:
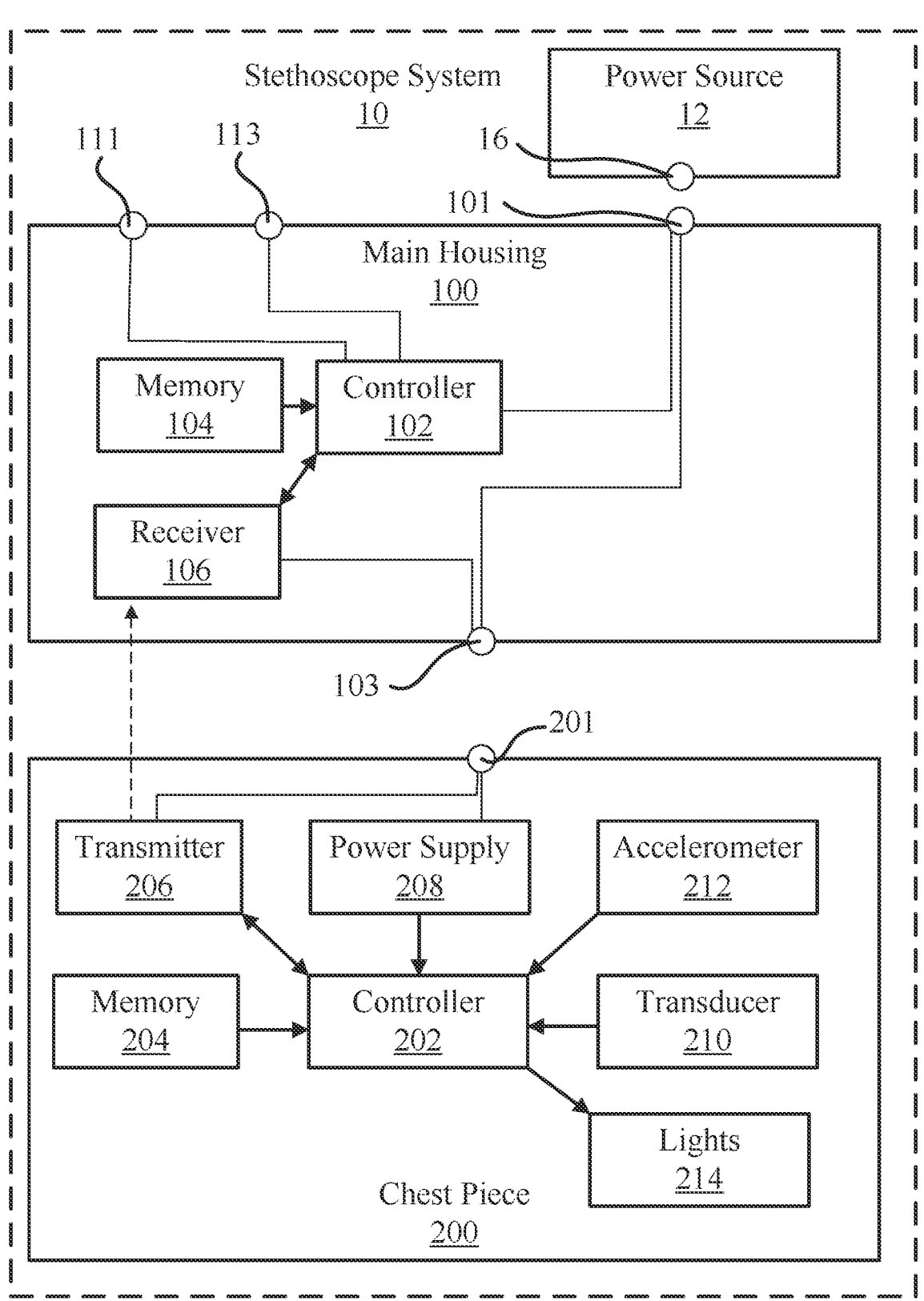
FIG. 1B illustrates a schematic view of the stethoscope system of FIG. 1A, in accordance with various embodiments.

Referring now to FIG. 1B, a schematic view of the stethoscope system 10 from FIG. 1A is illustrated with like numerals depicting like elements, in accordance with various embodiments. In various embodiments, the main housing 100 comprises a controller 102, and/or the chest piece 200 comprises a controller 202. In various embodiments, controllers 102, 202 may each be integrated into a microcontroller. In various embodiments, controllers 102, 202 may each be configured as a central network element or hub to access various systems and components of stethoscope system 10. Controllers 102, 202 may each comprise a network, computer-based system, and/or software components configured to provide an access point to various systems and components of stethoscope system 10. In various embodiments, controllers 102, 202 may each comprise a processor. In various embodiments, controllers 102, 202 may each be implemented in a single processor. In various embodiments, controllers 102, 202 may each be implemented as and may include one or more processors and/or one or more tangible, non-transitory memories and be capable of implementing logic. Each processor can be a general purpose processor, a digital signal processor (DSP), an application specific integrated circuit (ASIC), a field programmable gate array (FPGA) or other programmable logic device, discrete gate or transistor logic, discrete hardware components, or any combination thereof. Controllers 102, 202 may each comprise a processor configured to implement various logical operations in response to execution of instructions, for example, instructions stored on a non-transitory, tangible, computer-readable medium (e.g., memory 104 for controller 102 and/or memory 204 for controller 202) configured to communicate with controllers 102, 202.

System program instructions and/or controller instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The main housing 100 further comprises a receiver 106. The receiver 106 is in electrical communication with the controller 102. In various embodiments, the main housing 100 comprises a transceiver (e.g., a Bluetooth® low energy transceiver) having the receiver 106 and a transmitter. The present disclosure is not limited in this regard. In various embodiments, the main housing 100 further comprises a first audio connector 111 and a second audio connector 113. The first audio connector 111 is configured to couple to a first earbud (e.g., earbud 112) and the second audio connector 113 is configured to couple to a second earbud (e.g., earbud 114). In various embodiments, the audio connectors 111, 113 may comprise an electrical connector (e.g., an audio jack), configured to couple to an electrical connector (e.g., an adapter) of a wired earbud. In various embodiments, the audio connectors 111, 113 may comprise an electrical connector (e.g., a socket) configured to receive a port of a wireless earbud (e.g., to connect the wireless earbud to a power source such as the power source 12 for charging when not in use). In various embodiments, the audio connectors 111, 113 may be replaced with a direct wired connection from the controller 102 to the earbuds 112, 114 from FIG. 1A. The present disclosure is not limited in this regard.

The chest piece 200 further comprises a transmitter 206, a power supply 208, and a transducer 210. In various embodiments, the chest piece 200 comprises a transceiver (e.g., a Bluetooth® low energy transceiver) having the transmitter 206 and a receiver. The present disclosure is not limited in this regard. The controller 202 is in electrical communication with the transmitter 206, the power supply, 208, and the transducer 210. The transmitter 206 of the chest piece 200 is configured for electronic (e.g., wireless) communication with the receiver 106 of the main housing. In this regard, in the operable state, the controller 202 is configured to receive auscultation data (e.g., auscultation signals) from the transducer 210, convert the auscultation data into digital data (e.g., digital signals), and send the digital data to the transmitter 206 for wireless transmission to the receiver 106. In response to the receiver 106 receiving the digital data, the receiver 106 sends the digital data to the controller 102 of the main housing 100, the controller 102 then sends the digital data to the earbuds 112, 114 from FIG. 1A (or converts the digital data to analog data and then sends the analog data to the earbuds 112, 114 from FIG. 1A), in various embodiments. The present disclosure is not limited in this regard.

In various embodiments, the chest piece 200 further comprises an accelerometer 212 and lights 214 in electrical communication with the controller 202. Based on data received from the accelerometer 212, the controller 202 may be configured to determine whether the chest piece 200 is in use, or not in use. For example, in response to the controller 202 receiving data from the accelerometer 212 for a threshold time period (e.g., three minutes) of little to no movement, the controller 202 may command the lights 214 to turn off for power savings. The lights 214 may be configured for indicating an operating mode of the stethoscope system 10 as described further herein.

In response to coupling the power source 12 to the main housing 100, the power source 12 may be electrically coupled to a controller 102 of the main housing 100 and/or a controller 202 of the chest piece 200. In this regard, in response to coupling the power source 12 to the main housing 100, the power source 12 may be electrically coupled to a controller 102 of the main housing 100 and/or a power supply 208 of the chest piece 200. The power source 12 is configured to supply electrical power to the controller 102 of the main housing 100 in an operable state. In a fully assembled state, the power source 12 may be further configured to charge the power supply 208 of the chest piece 200. In various embodiments, power supply 208 of the chest piece 200 may be configured to be charged via an external charger (e.g., for more rapid charging).

Figure 3B:
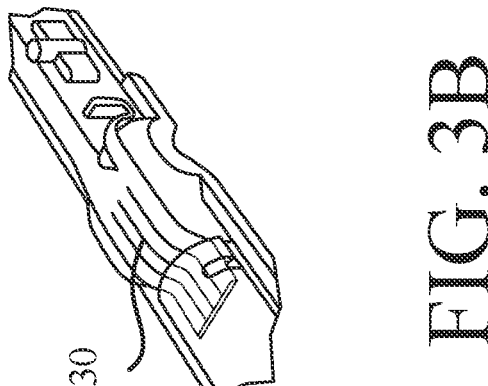
FIG. 3B illustrates a perspective detail view of the portion of the neck strap from FIG. 3A, in accordance with various embodiments.
Figure 3A:
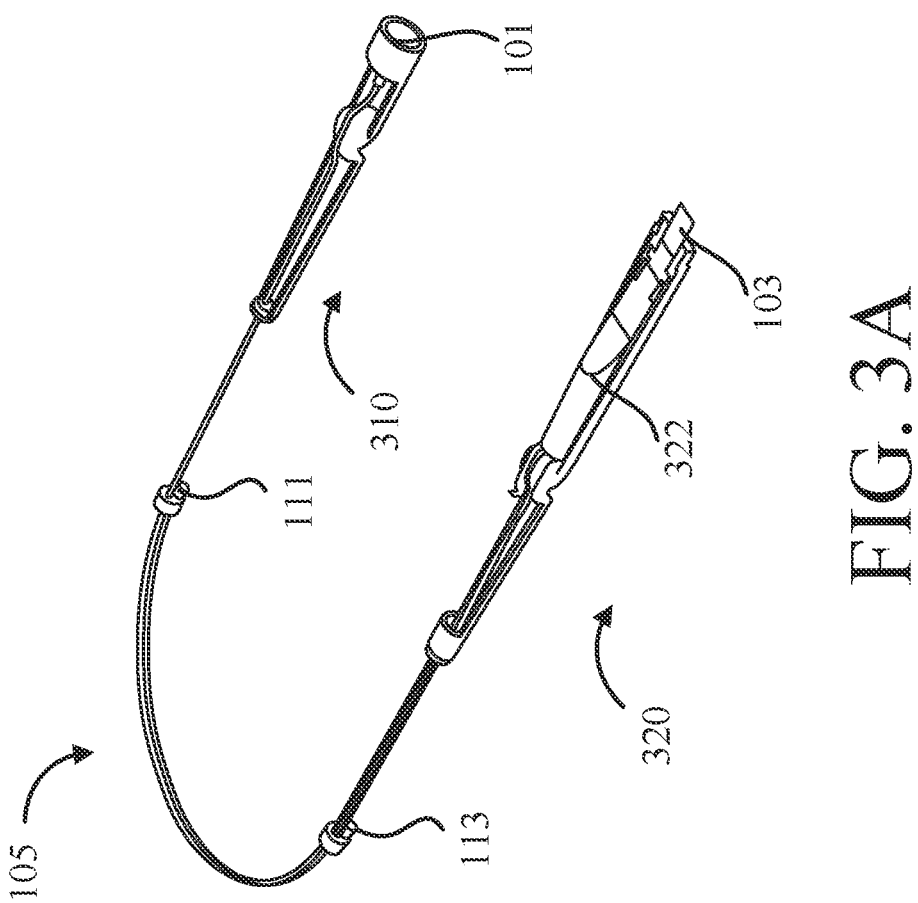
FIG. 3A illustrates a perspective view of a portion of a neck strap for a stethoscope system, in accordance with various embodiments.

Referring now to FIGS. 3A and 3B, a perspective view (FIG. 3A), and a perspective detail view (FIG. 3B) of the neck strap 105 with the case 110 removed for clarity is illustrated, in accordance with various embodiments. The neck strap 105 comprises a first housing 310 and a second housing 320. The first housing 310 may comprise the first electrical connector 101 disposed therein. The second housing 320 may comprise a main printed circuit board (PCB) 322. The main PCB 322 may comprise various components of the main housing 100 shown in FIG. 1B (e.g., the controller 102, memory 104, receiver 106, and any other electrical components), in accordance with various embodiments. The main PCB 322 is electrically coupled to the second electrical connector 103, which is configured to electrically couple to the electrical connector 201 of the chest piece 200 from FIGS. 1A-B.

In various embodiments, based on the electrical configuration desired for the neck strap 105, any number of conductors 330 (e.g., eleven conductors) may be coupled to the main PCB 322 (e.g., via soldering or the like), extend to various components (e.g., audio connectors 111, 113, a button PCB for volume adjustment, the first electrical connector 101, etc.). In various embodiments, any number of conductors may be coupled to the button PCB (e.g., three conductors). The present disclosure is not limited in this regard.

Figure 4A:
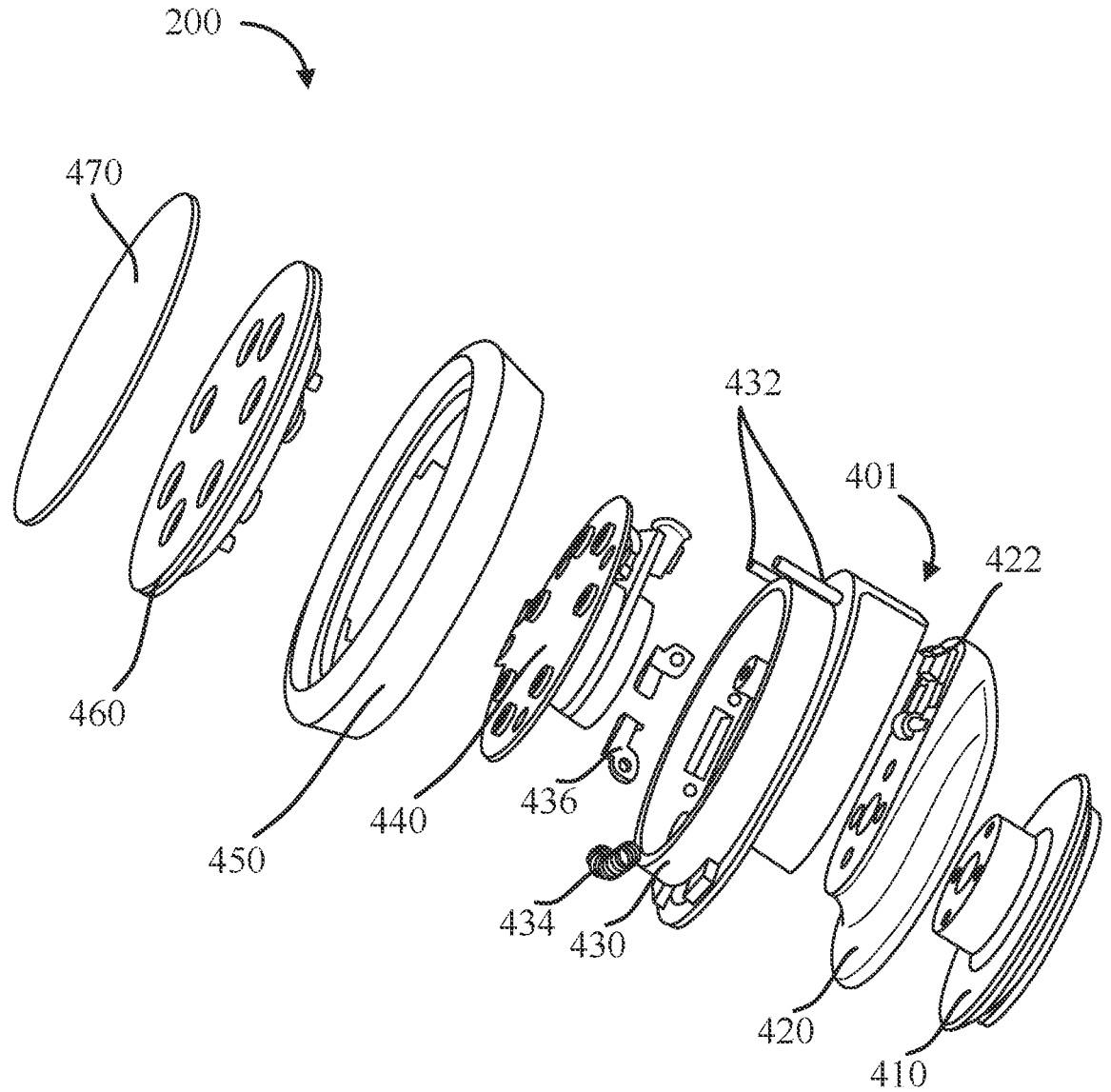
FIG. 4A illustrates a perspective exploded view of a chest piece, in accordance with various embodiments.

Referring now to FIG. 4A, a perspective exploded view of the chest piece 200 is illustrated, in accordance with various embodiments. The chest piece 200 comprises a cable retention assembly 401. In various embodiments, the cable retention assembly 401 includes the lower housing 420 and a biasing mechanism 422. The cable retention assembly 401, as described further herein, is configured to compress in response to a cable being inserted into a port and apply a retention force against a surface of the cable while the cable is coupled to the chest piece 200. In this regard, the cable retention assembly 401 is configured to retain the cable in the electric port during operation. For example, the biasing mechanism 422 is configured to apply a retention force to a cable (e.g., neck strap 105 from FIG. 1A) to retain an electrical connector (e.g., second electrical connector 103), within the electrical connector (e.g., electrical connector 201 of FIG. 1A) of the chest piece 200. In this regard, the connection between the chest piece 200 and the main housing 100 from FIG. 1B may be secure, which may prevent degradation of the electrical connection over time, in accordance with various embodiments In various embodiments, the chest piece 200 further comprises a bell 410 (e.g., a bell and a transducer such as a microphone), the lower housing 420, an upper housing 430, a printed circuit board assembly 440, a rotary ring 450, a retainer assembly 460, and a cap 470.

The bell 410 is disposed at a first axial end of the chest piece 200. The bell 410 includes a diaphragm. The diaphragm may be configured to interface with the skin of a patient during use of the stethoscope system 10 from FIGS.

1A-B. The bell 410 is configured to be coupled to the lower housing 420 and the upper housing 430.

In various embodiments, the upper housing 430 is configured to receive the printed circuit board assembly 440 therein. In this regard, the upper housing 430 secures and protects the printed circuit board assembly 440 from an external environment. In various embodiments, the upper housing 430 is configured to interface with the rotary ring 450. As described further herein, the rotary ring 450 may be operably coupled to the printed circuit board assembly 440. In this regard, in response to rotating the rotary ring 450 relative to the upper housing 430, the controller 202 from FIG. 1B of the printed circuit board assembly 440 may transition from a first mode (e.g., a mode configured to detect heart sounds) to a second mode (e.g., a mode to detect lung sounds).

The printed circuit board assembly 440 comprises various components from the schematic view of the chest piece 200 in FIG. 1B. For example, the printed circuit board assembly 440 may comprise controller 202, memory 204, transmitter 206, power supply 208, transducer 210, accelerometer 212 and/or lights 214 from FIG. 1B (e.g., light emitting diodes (LEDs) or the like), in accordance with various embodiments. However, the present disclosure is not limited in this regard. For example, the transducer 210 may be disposed in the bell and electrically coupled to the printed circuit board assembly 440, in accordance with various embodiments.

The retainer assembly 460 comprises a plurality of lights 214 from FIG. 1B (e.g., a light pipe pod, light pipes, etc.) and a gasket. The gasket can facilitate a smooth interface with a mating component. The light pipe pod and the light pipes are configured to light up in response to the controller 202 from FIG. 1B opening and closing electrical switches or the like. In this regard, the controller 202 from FIG. 1B is configured to activate a set of lights in the lights 214 from FIG. 1B in response to a setting (or mode) being selected as described previously herein.

The cap 470 comprises a polymeric material. For example, in various embodiments, the cap 470 can be formed by an over molding process of a soft thermoplastic elastomer (TPE). Although described herein as comprising a TPE material, the present disclosure is not limited in this regard, and various polymeric materials may be envisioned by one skilled in the art. In various embodiments, the cap 470 comprises a transparent membrane. In this regard, the lights 214 of the retainer assembly 460 positioned under the transparent membrane can be seen based on a respective mode of operation as described herein.

In various embodiments, the chest piece 200 further comprises operating rods 432, limit switches 434 and hammers 436. The operating rods 432 can be coupled to (loosely or otherwise) the upper housing 430. The operating rods 432 can serve as guides for the rotary ring 450 during operation of the chest piece 200. The limit switches 434 can be used to detect the presence of the rotary ring 450. In this regard, in response to a limit switch in the limit switches 434 detecting a presence of the rotary ring 450, the limit switch sends a signal to the controller 202 from FIG. 1B, and the controller sets a mode of the chest piece 200 as described previously herein. In this regard, the chest piece 200 can be configured to detect heart sounds, lung sounds or the like based on a mode being selected and corresponding to a respective limit switch being engaged (i.e., detecting a presence of the rotary ring 450).

Figures 4B, 4C:
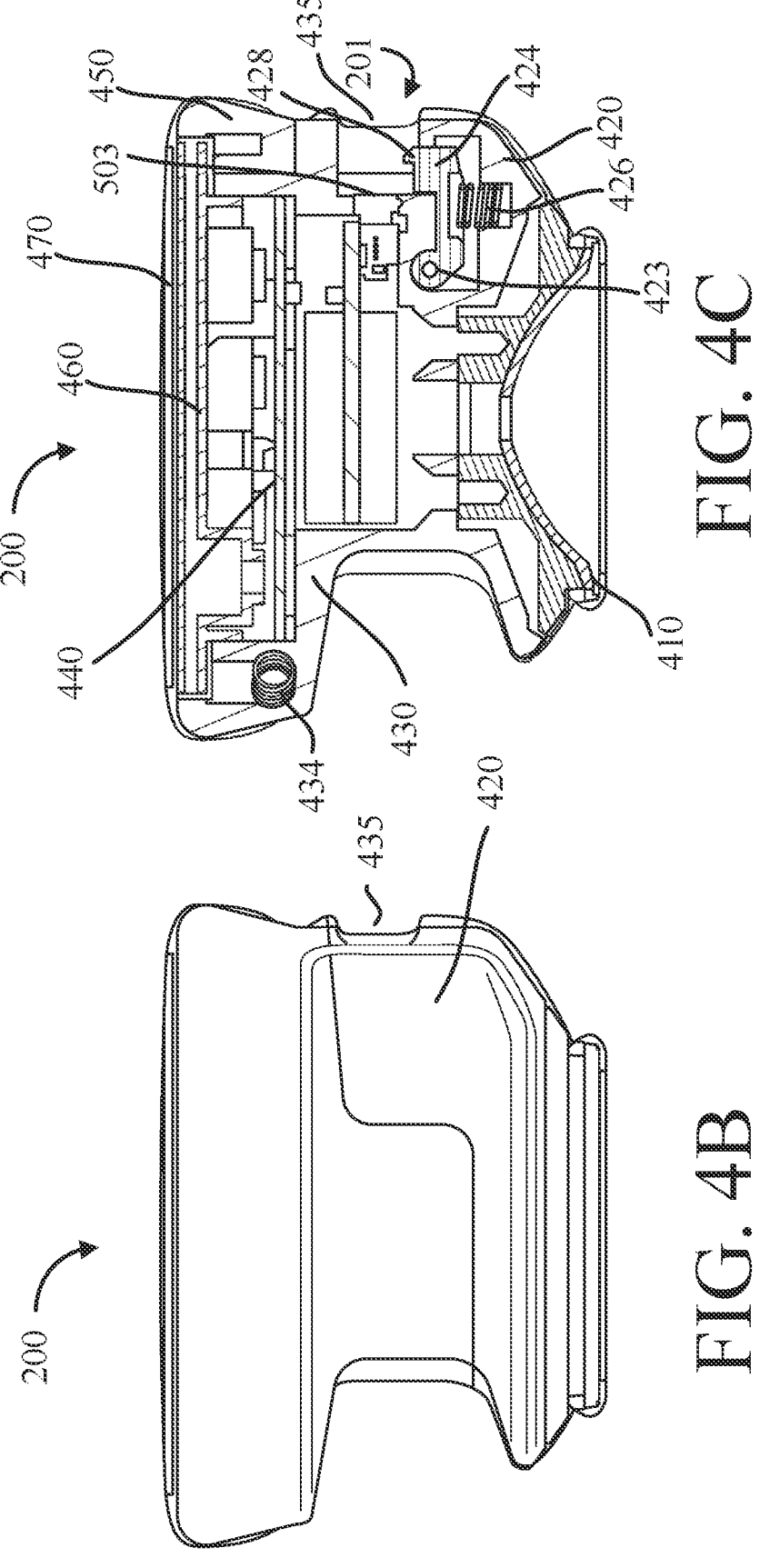
FIG. 4B illustrates a side view of the chest piece from FIG. 4B, in accordance with various embodiments.
FIG. 4C illustrates a cross-sectional view of the chest piece from FIG. 4A, in accordance with various embodiments.

Referring now to FIGS. 4B and 4C, a side view (FIG. 4B) and a cross-sectional view (FIG. 4C) of the chest piece 200 is illustrated, with like numerals depicting like elements, in accordance with various embodiments. In various embodiments, the cable retention assembly 401 of the chest piece 200 comprises a biasing mechanism 422. The biasing mechanism 422 an comprise a latch 424 and a spring 426. The latch 424 is pivotably coupled to the lower housing 420. The spring 426 can be disposed in a recess defined by the lower housing 420 and interface with a bottom surface of the latch 424. In various embodiments, the spring 426 is a compression spring. In this regard, the spring 426 is configured to apply a retention force to the latch 424 in a default state. In various embodiments, the cable retention assembly 401 further comprises a protrusion 428 extending from the latch 424 into an opening 435 defined between the upper housing 430 and the lower housing 420. In various embodiments, the protrusion 428 includes a lead-in chamfer. In this regard, in response to a cable contacting the lead-in chamfer of the protrusion 428, the latch 424 will pivot about a pivot axis defined by a shaft 423 of the biasing mechanism 422. In response to the latch 424 pivoting about the pivot axis defined by the shaft 423, the spring 426 compresses further than the default state. In an installed state, the cable will experience a retention force from the protrusion 428 of the latch 424 on a bottom surface of the cable. In this regard, the electrical connector 103 of the neck strap in a stethoscope system 10 from FIG. 1A can be sufficiently secured within the chest piece 200 to hold and/or charge the chest piece 200 while the chest piece 200 is not in use.

Figure 5:
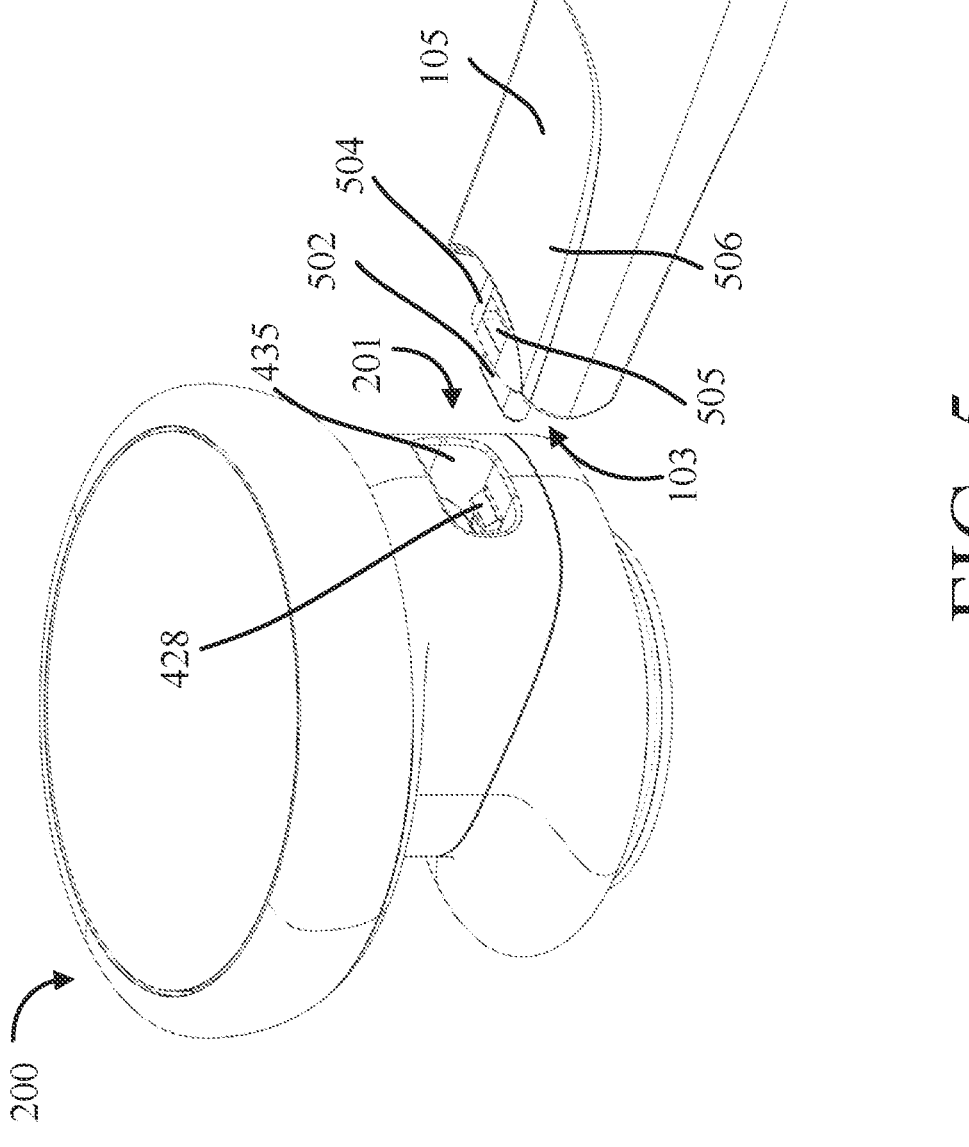
FIG. 5 illustrates a perspective view of a neck strap and a chest piece, in accordance with various embodiments.

Referring now to FIG. 5, a perspective view of the chest piece 200 and the neck strap 105 are illustrated, with like numerals depicting like elements, in accordance with various embodiments. In various embodiments, the electrical connector 103 of the neck strap 105 comprises a male conductor element 502 extending axially from a port cable jacket 504. The port cable jacket 504 extends from a main cable jacket 506. The port cable jacket 504 is smaller in cross sectional area relative to the main cable jacket 506. In various embodiments, the port cable jacket 504 is complimentary in shape to the opening 435 of the chest piece 200. In this regard, the port cable jacket 504 and the male conductor element 502 are configured to be inserted into the opening 435 to electrically couple the male conductor element 502 to the electrical connector 201 of the chest piece 200 from FIG. 1B (e.g., female conductor element 503 from FIG. 4C), as described previously herein.

In various embodiments, the port cable jacket 504 comprises a recess 505. In various embodiments, the recess 505 can be complimentary in shape to the protrusion 428. In this regard, the recess 505 can be configured to receive the protrusion 428 during assembly. Thus, the recess 505 can facilitate securing the chest piece 200 to the neck strap 105 via the cable retention assembly 401, in accordance with various embodiments.

Figure 6A:
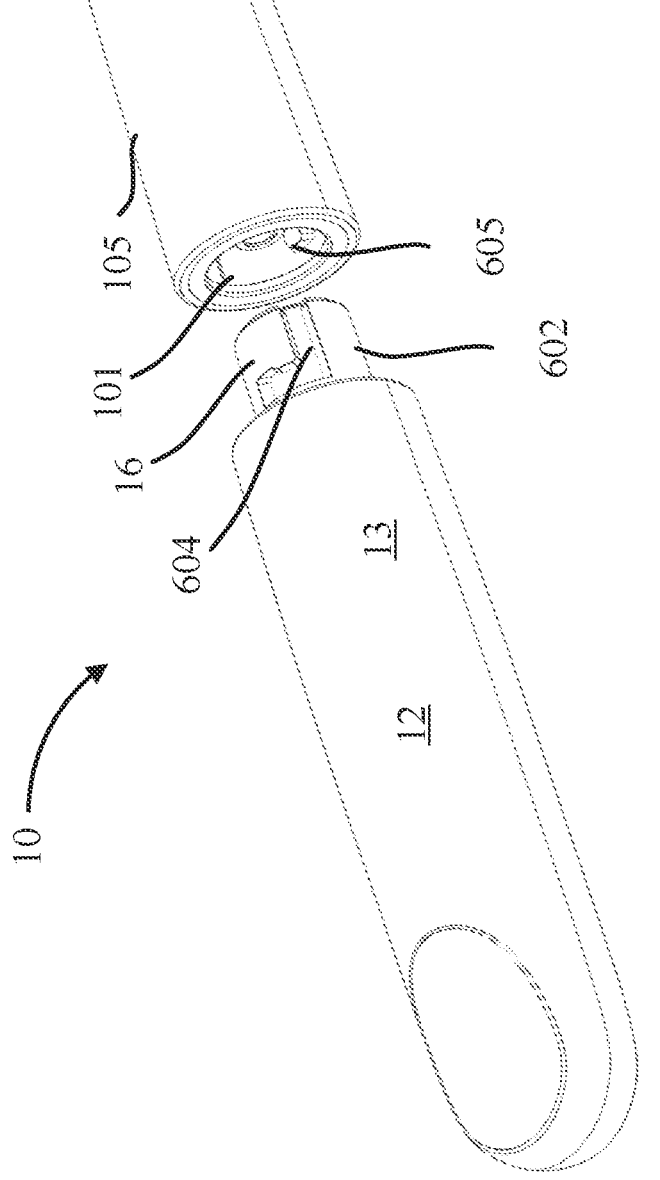
FIG. 6A illustrates a perspective view of a power source and a neck strap, in accordance with various embodiments.
Figure 6B:
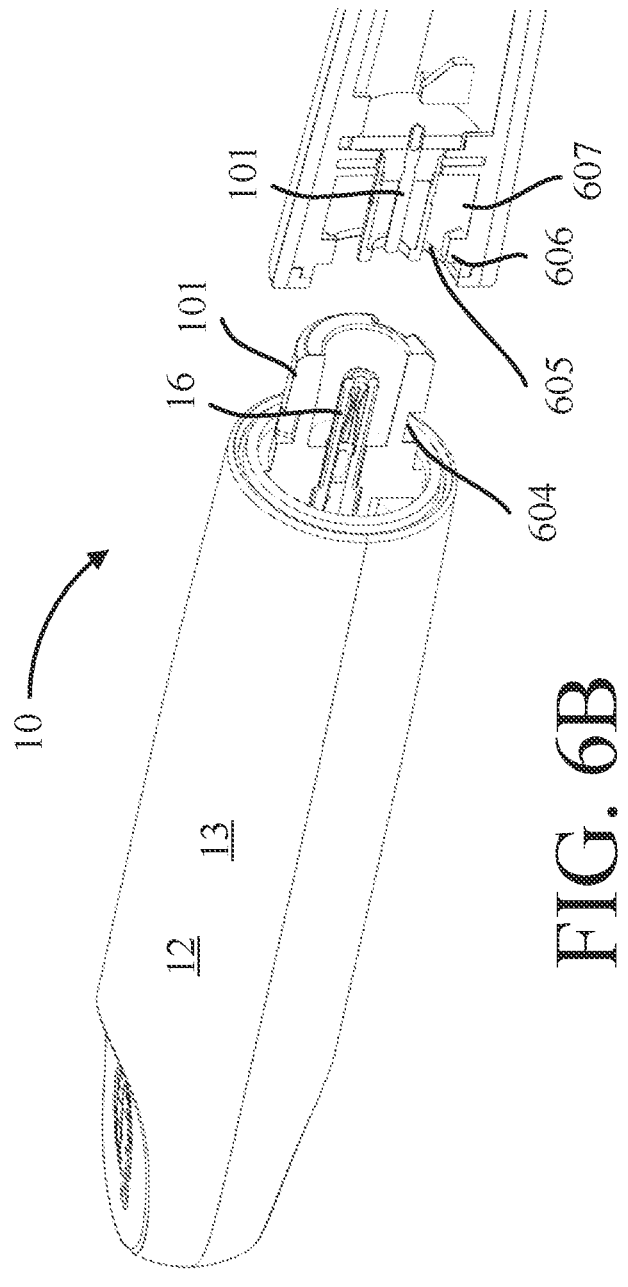
FIG. 6B illustrates a perspective cross-sectional view of a power source and a neck strap, in accordance with various embodiments.

Referring now to FIG. 6A-C, a perspective view (FIG. 6A) and perspective cross-sectional view (FIG. 6B) of a power source 12 and a neck strap 105 of a stethoscope system 10 from FIG. 1A during assembly is illustrated, in accordance with various embodiments. In various embodiments, the electrical connector 16 comprises a port cable jacket 602. The port cable jacket 602 comprises a cross-sectional diameter that is smaller than a cross-sectional diameter of the housing 13 of the power source. In this regard, the port cable jacket 602 is configured to be received within an aperture 605 of the neck strap 105. The aperture 605 corresponds to the electrical connector 101 configured to be electrically coupled to the electrical connector 16 of the power source 12.

In various embodiments, the port cable jacket 602 comprises a groove 604 disposed therein. The groove 604 includes an axial portion and a circumferential portion. In this regard, the groove 604 is configured to interface with a protrusion 606 from a radially inner surface 607 of the aperture 605. In this regard, during assembly, the electrical connector 16 can be inserted into the electrical connector 101 and then the power source 12 can be rotated to lock the power source in place. In this regard, the power source 12 can remain electrically and physically coupled to the neck strap to provide a continuous power source to the neck strap 105 during operation, in accordance with various embodiments.

Figure 7:
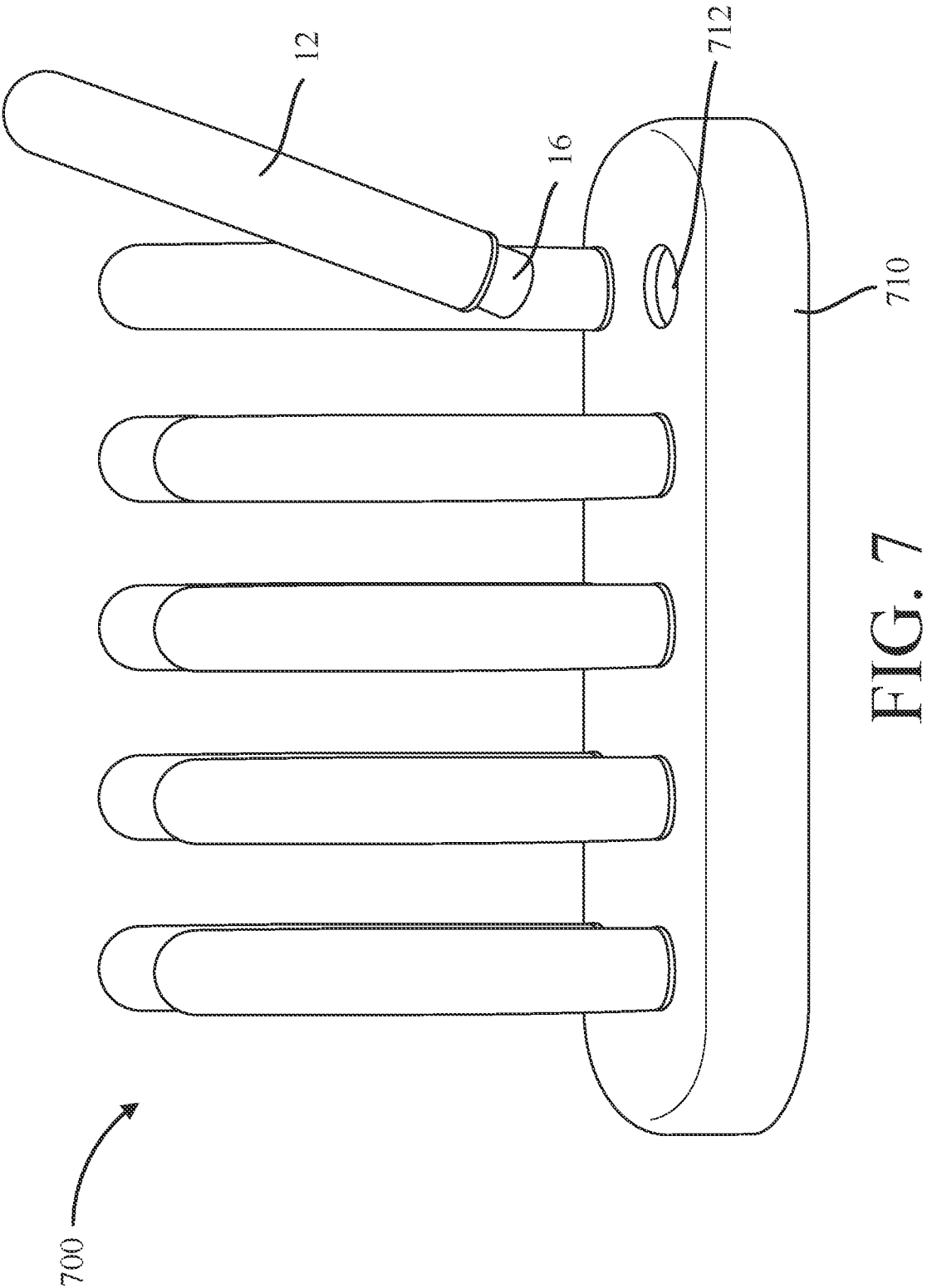
FIG. 7 illustrates a perspective view of a charging system for the power sources of a stethoscope system, in accordance with various embodiments.

Referring now to FIG. 7, a charging system 700 for a plurality of the power source 12 is illustrated, in accordance with various embodiments. In various embodiments, the charging system 700 comprises a base 710 with a plurality of charge ports 712. Each charge port in the plurality of charge ports 712 is configured to receive an electrical connector 16 of a power source 12 in the plurality of the power source 12. Thus, a power source 12 can be swapped out with ease after the battery is low or dead, facilitating a fast and efficient changing of batteries.

Although illustrated as including ten charge ports 712, the present disclosure is not limited in this regard. For example, any number of charge ports 712 in a base 710 of a charging system 700 for a stethoscope system 10 from FIG. 1A is within the scope herein. As described further herein, the stethoscope system can be utilized in a classroom environment, which can draw battery power faster than a typical stethoscope system. In this regard, having a plurality of power sources 12 being charged via charging station 700 can facilitate fast and easy changing of the power source 12 during a class or the like, in accordance with various embodiments.

Figure 8:
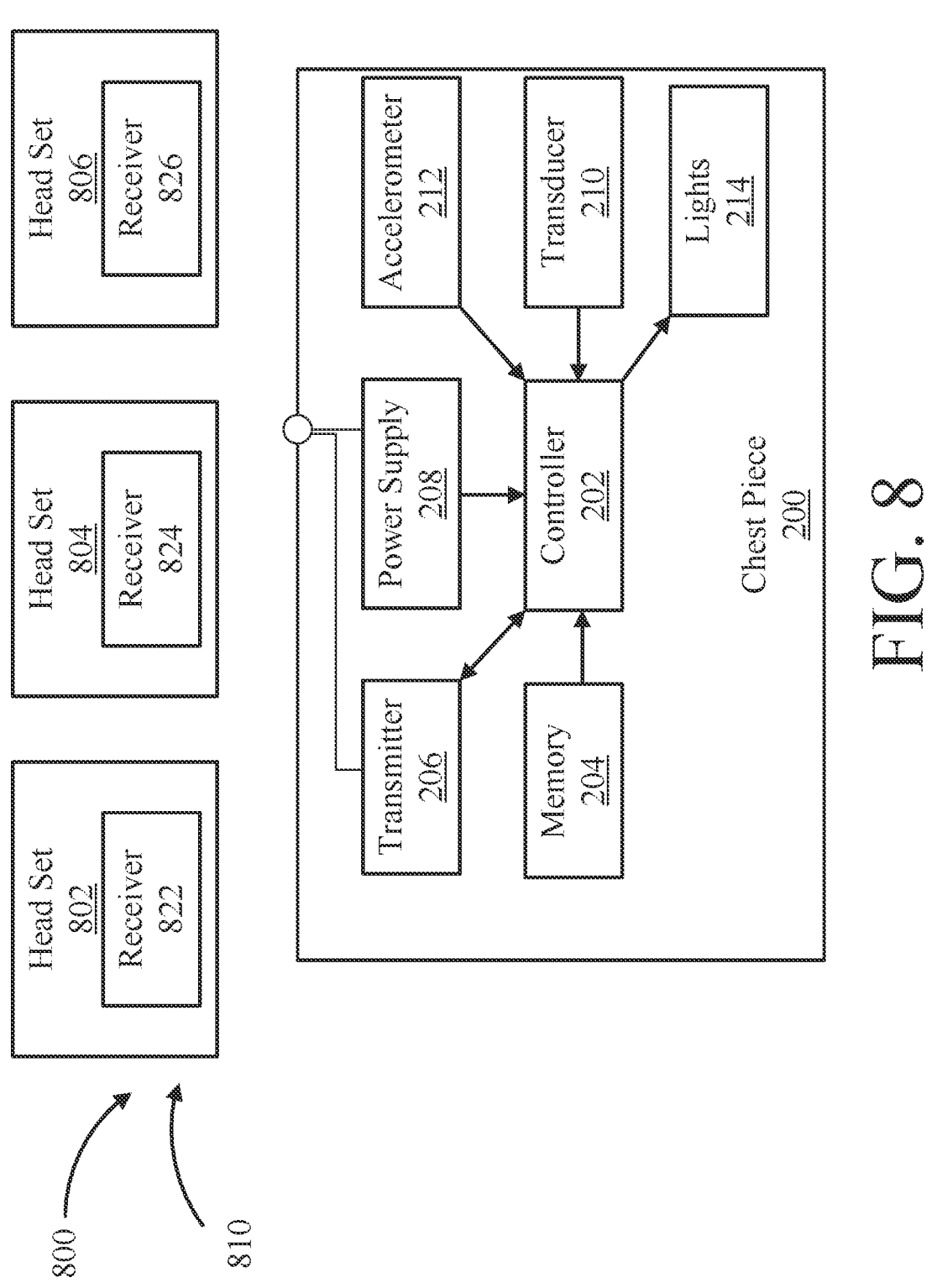
FIG. 8 illustrates a schematic view of a stethoscope system, in accordance with various embodiments.

Referring now to FIG. 8, a schematic view of a system 800 for teaching students about physiological sounds in real time is illustrated, with like numerals depicting like elements, in accordance with various embodiments. The system 800 includes the chest piece 200 and a plurality of headsets 810. Each headset (e.g., head set 802, 804, 806) in the plurality of headsets 810 comprises a respective receiver (e.g., receiver 822 for head set 802, receiver 824 for head set 804, and/or receiver 826 for head set 806). Although illustrated as comprising three headsets, the present disclosure is not limited in this regard.

As described previously herein, the chest piece 200 is configured to convert auscultation signals to digital signals for wireless transmission (e.g., via the transmitter 206) to the neck strap 105 for listening through the earbuds 112, 114 coupled to the neck strap 105 from FIG. 1B. In various embodiments, the chest piece 200 is further configured for wireless transmission of the converted auscultation signals to the plurality of headsets 810. In this regard, a student can be listening to the same auscultation signals as a teacher during a class by utilizing the system 800 in accordance with various embodiments. In addition to the plurality of headsets 810, the converted auscultation signals can be transmitted to a computer or the like for later study or for use later by students when reviewing notes. In this regard, the system 800 facilitates greater learning of medical students by real time transmission of signals from a stethoscope being supplied to all students at once.

Referring now to FIG. 9, a method 900 for using a stethoscope system (e.g., stethoscope system 10, 800) is illustrated, in accordance with various embodiments. The method 900 comprises draping a neck strap 105 around a neck of a user 902. The neck strap 105 extends from a first end to a second end as illustrated in FIG. 1B. The neck strap 105 can be coupled to a power source 12 and a chest piece 200. The neck strap 105 can provide a convenient place to store the chest piece comfortably while not in use and charge the chest piece 200 while not in use.

In various embodiments, the method 900 further comprises de-coupling the chest piece 200 from the second end of the neck strap 105 (step 904) and selecting an operating mode for the chest piece 200 (step 906). In various embodiments, the mode can be selected as previously disclosed herein. For example, a rotary ring 450 of the chest piece can be rotated until a limit switch of the limit switches 434 corresponding to the mode detects the presence of the rotary ring 450.

In various embodiments, the method 900 further comprises placing the chest piece on a skin of a patient (step 908). In various embodiments, the bell 410 can be disposed on the skin of the user. In this regard, the bell 410 and microphone can convert the auscultation signals into a small electrical current that is transmitted to the controller 202, converted to digital data as described previously herein, and transmitted from a transmitter 206 in the chest piece 200 to a plurality of receivers (e.g., receivers 822, 824, 826 of headsets 802, 804, 806) (step 910).

In various embodiments, the method 900 further comprises de-coupling a first power source in response to the first power source having low power (step 912) and coupling a second power source form a charging system to the neck strap (step 914). In this regard, as described previously herein, the power source can easily be swapped out with a charging power source from a charging station 700 as shown in FIG. 7. In various embodiments, the method 900 further comprises coupling the first power source to the charging system (step 916). Thus, the power source with low power can begin to recharge on the charging system 700.

Figure 10:
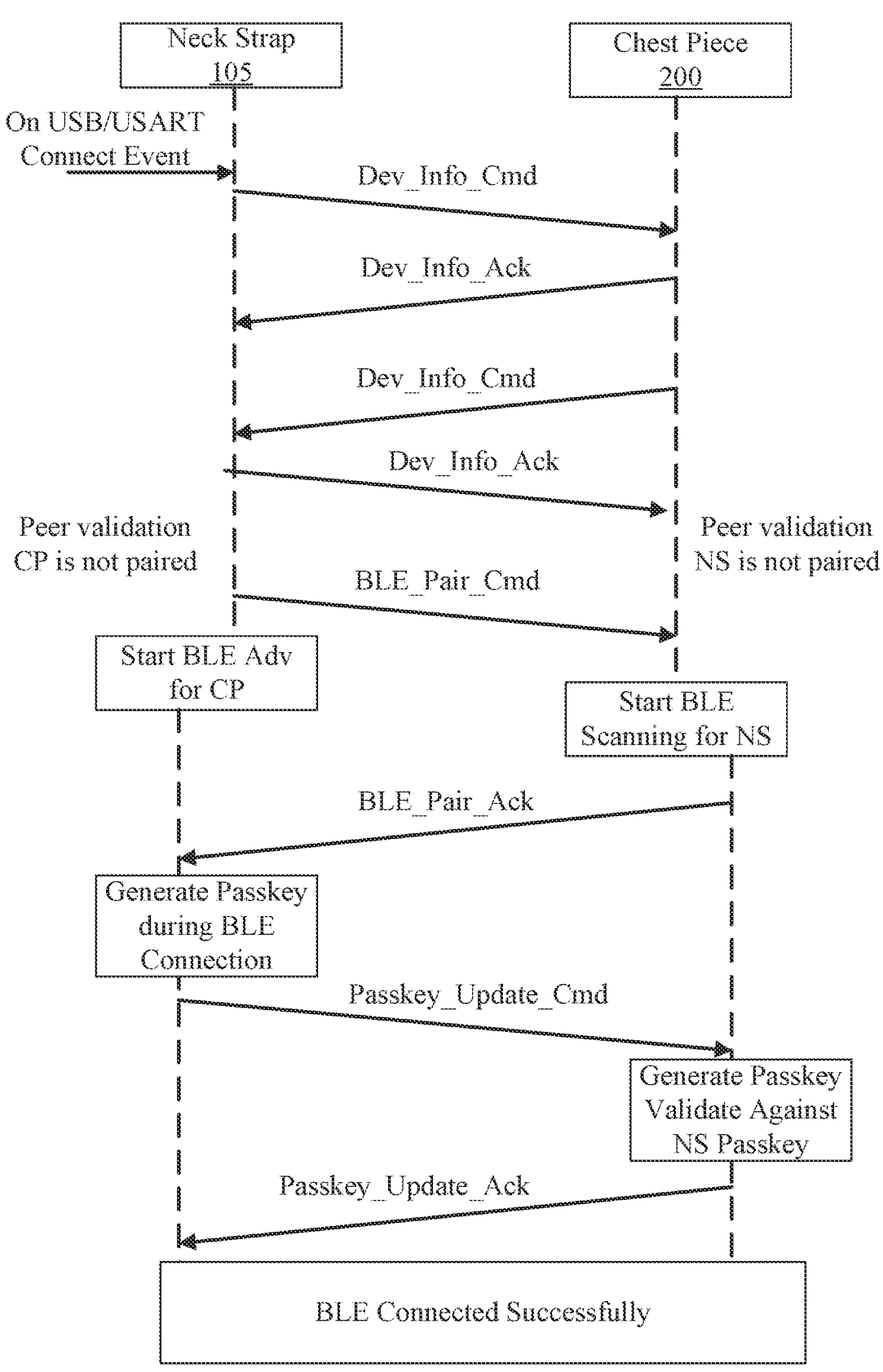
FIG. 10 illustrates a method of pairing a neck strap to a chest piece, in accordance with various embodiments.

Referring now to FIG. 10, a pairing process between the neck strap 105 and the chest piece 200 is illustrated, in accordance with various embodiments. The electromechanical connection between the chest piece 200 and neck strap 105 may age and wear over time leading to intermittent connections over the two-wire connection used to exchange key information and pair the chest piece 200 to the neck strap 105. To improve reliability, a forward error correction method as shown in FIG. 10 may be leveraged to detect m-type errors and correct n-type errors. For example, encoding the communication word such that there is a distance of 4 between codewords would allow correcting two bits (and possibly more with additional points to bits that are suspected to be in error). This would allow for improved user experience as the product ages by maintaining reliable communication between the chest piece 200 and neck strap 105 components.

With continued reference to FIG. 10, a pairing process can be initiated by neck strap 105 in response to being connected to the chest piece 200 (e.g., in response to coupling electrical connector 103 (e.g., a USB-C connector) to the electrical connector 201 (e.g., a USB-C port). In various embodiments, the electrical connectors 103, 201 each comprise a UART port. The UART ports of the chest piece 200 and the neck strap 105 are connected using side band signal pins of the USB-C connector, in accordance with various embodiments. The neck strap 105 can act like a master and initiate the communications with the chest piece 200 over UART. Although described herein as having the neck strap 105 act as the master, the present disclosure is not limited in this regard. For example, the chest piece 200 can act as the master and still be within the scope of this disclosure.

In various embodiments, the neck strap 105 sends various information over UART to the chest piece 200. For example, the neck strap 105 can send information including device type of the neck strap 105, a firmware version of the neck strap 105, a BLE mac address of the neck strap 105, and/or a paired device mac address, in accordance with various embodiments.

In various embodiments, the chest piece 200 verifies information from the neck strap 105 and confirms that the information is not corrupted & sends an acknowledgment of the information to the neck strap 105. After this, chest piece 200 also sends its device information to the neck strap 105 over UART (the format being same as above). Neck strap 105 can verify the information from the chest piece 200 and responds to the chest piece 200 with an acknowledgement of the information from the chest piece 200.

Neck strap 105 then determines whether the chest piece 200 is already paired with the neck strap 105 or not. For example, the neck strap 105 initiates the BLE pairing by transmitting a BLE pairing command to the chest piece 200 over UART, if it is not already paired. Neck strap 105 can also start BLE peripheral device and starts the BLE beacons only for the chest piece 200. In response to the chest piece 200 receiving the BLE pairing command, the chest piece 200 starts the BLE central device and starts scanning for BLE beacons meant for the chest piece 200.

In response to the chest piece 200 BLE central device finding the neck strap 105 peripheral beacon, the chest piece 200 initiates a BLE connection over a BLE channel. During the connection procedure, user authentication is required by the LE security module. Both devices generate 6 digit security passkeys independently. Although described herein as generating 6 digit security passkeys, the present disclosure is not limited in this regard. For example, any number of digits can be utilized for security passkeys and be within the scope of this disclosure.

Neck strap 105 then sends the 6-digit security passkey under passkey update command to the chest piece 200 over UART. Chest piece 200 then receives the passkey and verifies it against the passkey generated by it and sends back passkey acknowledgement to the neck strap 105 over UART. In this way the user authentication is achieved using an out of band UART communication channel.

On passkey verification, both devices (e.g., neck strap 105 and chest piece 200) continue the BLE connection procedure and generate Long Term Keys (LTK) and store them in flash under bonding procedure. These LTK's are used for future connection directly.

As used herein, "transmit" may include sending at least a portion of electronic data from one component to another. Additionally, as used herein, "data," "information," or the like may include encompassing information such as commands, queries, files, messages, data for storage, and the like in digital or any other form.

As used herein, "electronic communication" may comprise a physical coupling and/or non-physical coupling capable of enabling components to transmit and receive data. For example, "electronic communication" may refer to a wired or wireless protocol such as a CAN bus protocol, an Ethernet physical layer protocol (e.g., those using 10BASE-T, 100BASE-T, 1000BASE-T, etc.), an IEEE 1394 interface (e.g., FireWire), Integrated Services for Digital Network (ISDN), a digital subscriber line (DSL), an 802.11a/b/g/n/ac signal (e.g., Wi-Fi), a wireless communications protocol using short wavelength UHF radio waves and defined at least in part by IEEE 802.15.1 (e.g., the BLUETOOTH® protocol maintained by Bluetooth Special Interest Group), a wireless communications protocol defined at least in part by IEEE 802.15.4 (e.g., the ZIGBEE® protocol maintained by the ZigBee alliance), a cellular protocol, an infrared protocol, an optical protocol, or any other protocol capable of transmitting information via a wired or wireless connection.

One or more of the components discussed herein may be in electronic communication via a network. As used herein, the term "network" may further include any cloud, cloud computing system, or electronic communications system or method that incorporates hardware and/or software components. Communication amongst the nodes may be accomplished through any suitable communication channels, such as, for example, a telephone network, an extranet, an intranet, Internet, point of interaction device (personal digital assistant, cellular phone, kiosk, tablet, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using Internetwork Packet Exchange (IPX), APPLETALK® program, IP-6, NetBIOS, OSI, any tunneling protocol (e.g., IPsec, SSH, etc.), or any number of existing or future protocols. If the network is a public network, such as the internet, it may be advantageous to presume the network to be insecure and open to eavesdroppers. Specific information related to the protocols, standards, and application software utilized in connection with the Internet is generally known to those skilled in the art and, as such, need not be detailed herein.

Benefits, other advantages, and solutions to problems have been described herein regarding specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosures.

The scope of the disclosures is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A stethoscope system, comprising:
   a power source;
   a main housing comprising a neck strap extending from a first end to a second end, the first end configured to couple to the power source, the main housing comprising a first transceiver;
   a chest piece configured to removably couple to the second end of the neck strap, the chest piece comprising a second transceiver;
   a fully assembled configuration having the power source and the chest piece both coupled to the neck strap, the power source configured to charge a power supply in the chest piece in response to being in the fully assembled configuration; and
   an operable configuration having the power source coupled to the neck strap and the chest piece being de-coupled from the neck strap, the neck strap configured to wrap loosely around a user's neck, and the chest piece configured to convert auscultation signals to digital signals for wireless transmission from the second transceiver to the first transceiver.

2. The stethoscope system of claim 1, further comprising a plurality of headsets, the chest piece configured to wirelessly transmit the digital signals to the plurality of headsets in the operable configuration.

3. The stethoscope system of claim 1, wherein the chest piece is configured to transmit the digital signals to a plurality of transceivers.

4. The stethoscope system of claim 1, further comprising a charging system, the charging system including a plurality of charge ports, each charge port in the plurality of charge ports configured to receive the power source.

5. The stethoscope system of claim 4, further comprising a plurality of the power source, each power source in the plurality of the power source configured to charge in a respective charge port in response to not being in use.

6. The stethoscope system of claim 5, wherein any power source in the plurality of the power source is swappable with the power source in response to the power source running low on a state of charge.

7. A method of using a wireless stethoscope system, the method comprising:

draping a main housing comprising a neck strap around a neck of a user, the neck strap coupled to a power source on a first end and a chest piece on a second end, the main housing comprising a first transceiver and the chest piece comprising a second transceiver and the power source configured to charge a power supply in the chest piece in response to both being coupled to the neck strap;

de-coupling the chest piece from the second end;

selecting an operating mode for the chest piece;

placing the chest piece on a skin of a patient;

convert auscultation signals from the chest piece to digital signals; and transmitting the digital signals from the second transceiver to the first transceiver.

8. The method of claim 7, wherein the chest piece is configured to wirelessly transmit the digital signals to a plurality of headsets.

9. The method of claim 7, further comprising:

de-coupling the power source in response to the power source having low power; and coupling a second power source to the first end of the neck strap.

10. The method of claim 9, further comprising de-coupling the second power source from a charging station having plurality of power sources prior to coupling the second power source to the neck strap.

11. The method of claim 10, further comprising coupling the power source to the charging station.

12. The method of claim 7 further comprising transmitting the digital signals from the chest piece to a plurality of transceivers.

13. A method comprising:

providing a power source;

providing a main housing comprising a neck strap extending from a first end to a second end, the first end configured to couple to the power source, the main housing comprising a first transceiver;

providing a chest piece configured to removably couple to the second end of the neck strap, the chest piece comprising a second transceiver;

facilitating a fully assembled configuration having the power source and the chest piece both coupled to the neck strap, the power source configured to charge a power supply in the chest piece in response to being in the fully assembled configuration; and facilitating an operable configuration having the power source coupled to the neck strap and the chest piece being de-coupled from the neck strap, the neck strap configured to wrap loosely around a user's neck, and the chest piece configured to convert auscultation signals to digital signals for wireless transmission from the second transceiver to the first transceiver.

14. The method of claim 13 further comprising providing a plurality of headsets, the chest piece configured to wirelessly transmit the digital signals to the plurality of headsets in the operable configuration.

15. The method of claim 13, wherein the chest piece is configured to transmit the digital signals to a plurality of transceivers.

16. The method of claim 13 further comprising providing a charging system, the charging system including a plurality of charge ports, each charge port in the plurality of charge ports configured to receive the power source.

17. The method of claim 16 further comprising providing a plurality of the power source, each power source in the plurality of the power source configured to charge in a respective charge port in response to not being in use.

18. The method of claim 17, wherein any power source in the plurality of the power source is swappable with the power source in response to the power source running low on a state of charge.

* * * * *